United States Patent [19]

Mock

[11] Plant 4,135

[45] Oct. 25, 1977

[54] CHRYSANTHEMUM

[76] Inventor: Norman Mock, 1363 Murphy Ave., San Jose, Calif. 95131

[21] Appl. No.: 735,323

[22] Filed: Oct. 26, 1976

[51] Int. Cl.[2] ..... A01H 5/00
[52] U.S. Cl. ..... Plt./74
[58] Field of Search ..... Plt./74

*Primary Examiner*—Robert E. Bagwill

*Attorney, Agent, or Firm*—Boone, Schatzel, Hamrick & Knudsen

[57] ABSTRACT

A new variety of chrysanthemum plant originating as a seedling of the Red Rover (unpatented) and a miscellaneous yellow bloom, and characterized by its velvety yellow blooms, vigorous growth, 9 week response and persistence.

1 Drawing Figure

BACKGROUND OF THE NEW PLANT

The present invention comprises a new and distinct cultivar of chrysanthemum plant which is a seedling of a miscellaneous yellow chrysanthemum and the unpatented commercial cultivar known in the United States as Red Rover. The new cultivar was selected from the offspring of the aforementioned cross in October of 1973 in San Jose, Calif., and has been asexually reproduced by cuttings at the same location. The new cultivar has been found to retain its distinctive characteristics through successive propagations.

DESCRIPTION OF THE DRAWING

The accompanying drawing shows the unique characteristics of the new cultivar, the color being as nearly true as possible with color illustrations of this type. The photo shows the new cultivar in full bloom.

DESCRIPTION OF THE NEW PLANT

The new cultivar is a short day response plant and, when grown in the vicinity of San Jose, Calif., has a response time of 9 weeks. During the winter growing period the color of the blooms deepen.

In the description which follows, color references are made to the Munsell Book of Color, 1966 edition, published by the Munsell Color Company of Baltimore, Md.

Botanical classification: *Chrysanthemum morifolium.*

Bloom:
- *Size.*—Medium.
- *Fully expanded.*—4½ inches.
- *Borne.*—Singly on disbudded branches.
- *Stems.*—Short, normal.
- *Form.*—Round, planar.
- *Permanence.*—Hang on and dry.

Color:
- *Center of flower.*—Green-Yellow 2.5 GY 6/8.
- *Base of petals.*—Green-Yellow 5 GY 8/10.
- *Inside of petals.*—Yellow 7.5 Y 8.5/12.

- *Reverse of petals.*—Yellow 7.5 Y 8.5/10.
- *Tonality from a distance.*—Yellow 5 Y 8.5/14.
- *Discoloration.*—None.

Petals:
- *Texture.*—Thin and soft.
- *Appearance.*—Velvety/satiny.
- *Arrangement.*—Imbricated.
- *Persistence.*—Hang on and dry.
- *Fragrance.*—Slight, typical chrysanthemum.

Reproductive organs:
- *Stamen, anthers.*—Many, small.
- *Pollen.*—5 Y 8.5/14.
- *Arrangement.*—Regular around styles.
- *Styles.*—Columnar.
- *Length.*—Long.
- *Ovaries.*—Enclosed in calyx.

Plant:
- *Form.*—Pillar and herbaceous.
- *Growth.*—Vigorous, upright, branching of lateral buds.
- *Height.*—Approximately 28 inches, depending on culture.
- *Spread.*—None on single stem, 5 inches on single pinched plant.

Foliage:
- *Top side.*—Dark green 7.5 G 3/4.
- *Size.*—Medium.
- *Quantity.*—Abundant.
- *Shape.*—Lanceolate.
- *Texture.*—Velvety.
- *Ribs and veins.*—Ordinary.
- *Edge.*—Serrated.
- *Serration.*—Single, small.
- *Underside.*—Dark green, 7.5 G 4/4.
- *Stipules.*—Short, smooth.

I claim:

1. A new and distinct cultivar of chrysanthemum, substantially as described and pictured herein, characterized by its velvety yellow blooms, vigorous growth, 9 week response and persistence.

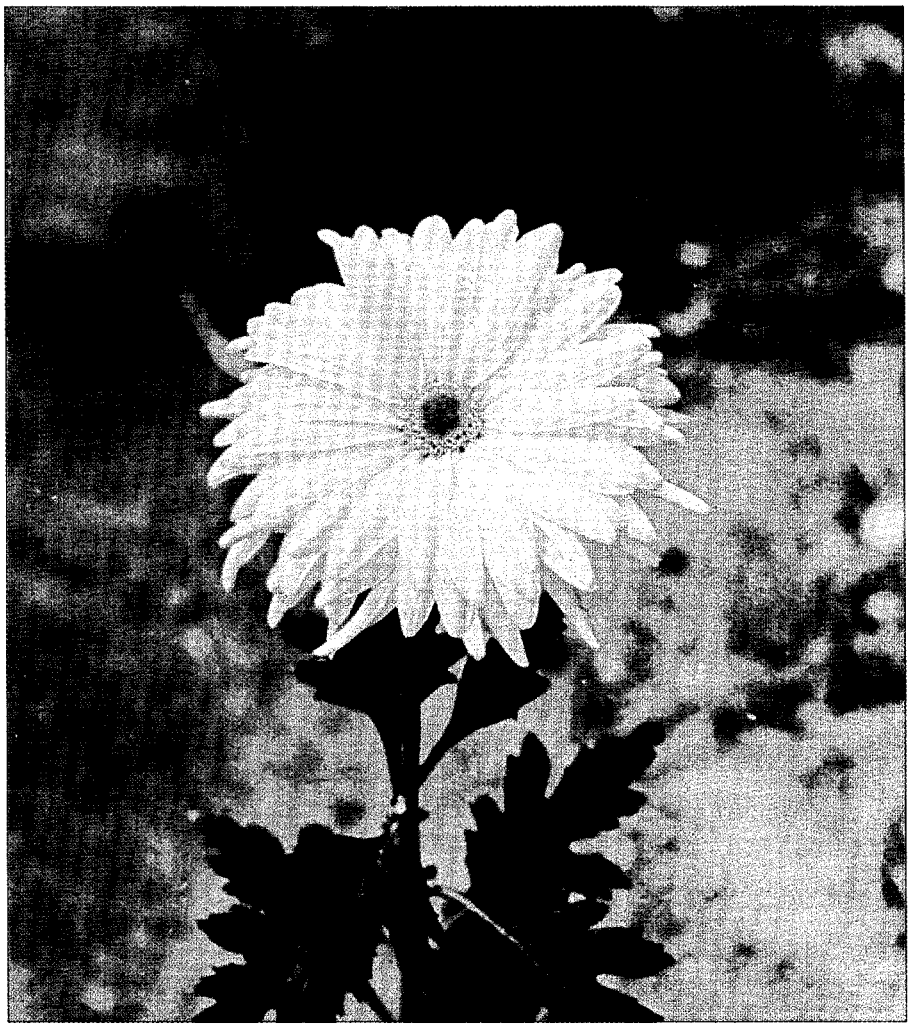

* * * * *